(12) United States Patent
Hernandez

(10) Patent No.: US 8,534,289 B2
(45) Date of Patent: Sep. 17, 2013

(54) APPARATUS FOR REDUCING SNORING

(76) Inventor: David Hernandez, Bronx, NY (US)

( * ) Notice: Subject to any disclaimer, the term of this patent is extended or adjusted under 35 U.S.C. 154(b) by 401 days.

(21) Appl. No.: 12/659,805

(22) Filed: Mar. 22, 2010

(65) Prior Publication Data

US 2011/0226261 A1    Sep. 22, 2011

(51) Int. Cl.
*A61F 5/56* (2006.01)

(52) U.S. Cl.
USPC ............................ 128/848; 602/902

(58) Field of Classification Search
USPC ............ 128/848, 859, 861, 862; 433/6; 602/902
See application file for complete search history.

(56) References Cited

U.S. PATENT DOCUMENTS

| | | | | |
|---|---|---|---|---|
| 2,857,909 | A * | 10/1958 | Johnson | 128/861 |
| 4,114,614 | A * | 9/1978 | Kesling | 128/861 |
| 4,173,219 | A * | 11/1979 | Lentine | 604/77 |
| 5,313,960 | A | 5/1994 | Tosami | |
| 5,829,441 | A * | 11/1998 | Kidd et al. | 128/848 |
| 5,868,138 | A | 2/1999 | Halstrom | |
| 6,055,986 | A * | 5/2000 | Meade | 128/848 |
| 6,516,805 | B1 | 2/2003 | Thornton | |
| 6,983,752 | B2 * | 1/2006 | Garabadian | 128/848 |
| 7,810,503 | B2 * | 10/2010 | Magnin | 128/848 |
| 8,166,976 | B2 * | 5/2012 | Webster et al. | 128/848 |
| 2008/0035160 | A1 * | 2/2008 | Woodson et al. | 128/860 |
| 2008/0099029 | A1 | 5/2008 | Lamberg | |
| 2008/0138766 | A1 * | 6/2008 | Jansheski | 433/140 |
| 2009/0090371 | A1 * | 4/2009 | Toussaint | 128/848 |

* cited by examiner

*Primary Examiner* — Patricia Bianco
*Assistant Examiner* — Raymond E Harris
(74) *Attorney, Agent, or Firm* — Seyfarth Shaw LLP; John C. Serio

(57) ABSTRACT

A mouthpiece for reducing snoring is provided. The mouthpiece includes an upper guard configured to fit over the upper teeth of a user, a lower guard configured to fit over the lower teeth of the user, a spacer assembly provided between the upper guard or the lower guard to provide an air passage at a middle section of the mouthpiece, a first adjustable assembly attached to the left side of the upper guard and the left side of the lower guard, and a second adjustable assembly attached to the right side of the upper guard and the right side of the lower guard. The first adjustable assembly and the second adjustable assembly are operable to move the lower guard relative to the upper guard.

17 Claims, 4 Drawing Sheets

APPARATUS FOR REDUCING SNORING

FIELD OF THE INVENTION

The present invention relates to a device for reducing snoring. More particularly, the present invention relates to a mouthpiece having an adjustable mechanism for reducing snoring.

BACKGROUND

Snoring usually occurs when the airway of a sleeping person is restricted. Snoring can irritate those around the snorer. In some situations, the snorer may wish to reduce the snoring.

DETAILED DESCRIPTION OF THE EMBODIMENTS

Figure 1:
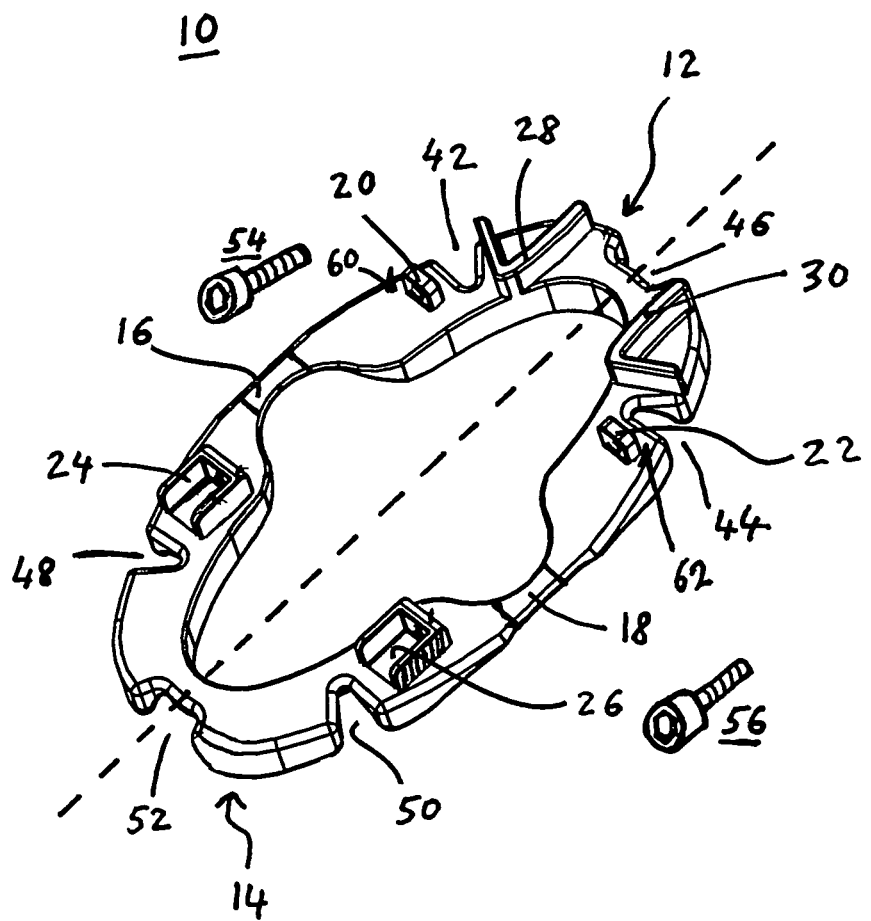
FIG. 1 is a bottom perspective view of a mouthpiece in an open position prior to being assembled according to an embodiment of the present invention.

Embodiments of the invention will now be described with reference to the drawing figures. To facilitate the description, a numeral designating an element in one figure will represent the same element in any other figure.

The present invention relates to a mouthpiece device for a user to use during sleep to reduce snoring. The mouthpiece includes an upper guard for the upper teeth and a lower guard for the lower teeth of a user. The upper and lower guards include notches to allow the mouthpiece to expand or contract to fit the widths of the user's jaws. The mouthpiece also includes an adjustable assembly on each of two sides of the mouthpiece, to allow the user to adjust the position of the lower guard relative to the upper guard. Using the adjustable assemblies, the user may adjustably bring the lower guard out toward the front of the mouthpiece, relative to the upper guard. With the lower guard being brought outward relative to the upper guard, the lower jaw of the user is brought out toward the front of the mouth. Because the lower jaw is brought outward, the normally restricted airway of the user opens during sleep. With the airway opens up, any resonance in the airway that causes snoring is reduced. As a result, the snoring of the mouthpiece user is reduced or eliminated.

Figure 2:
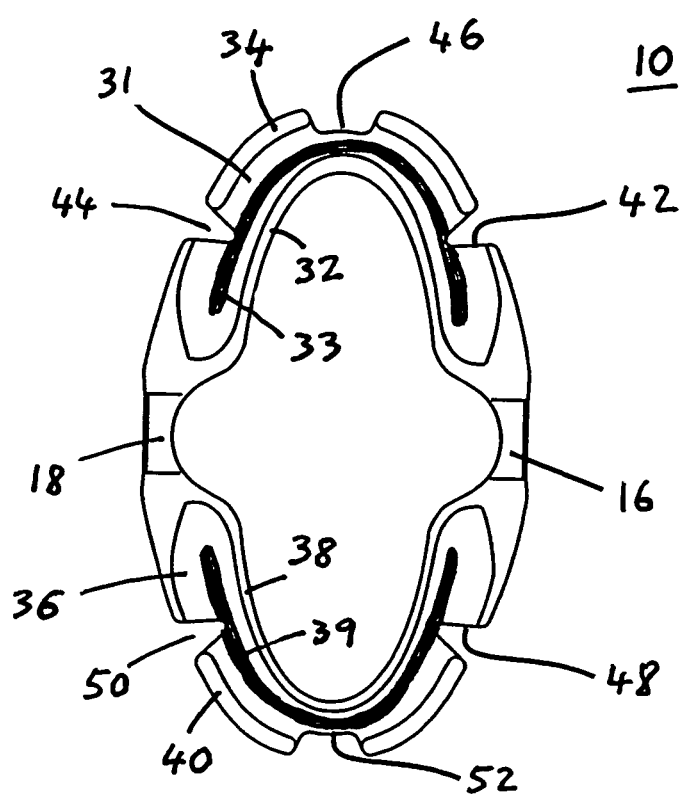
FIG. 2 is a top plan view of the mouthpiece of FIG. 1 according to an embodiment of the present invention.
Figure 3:
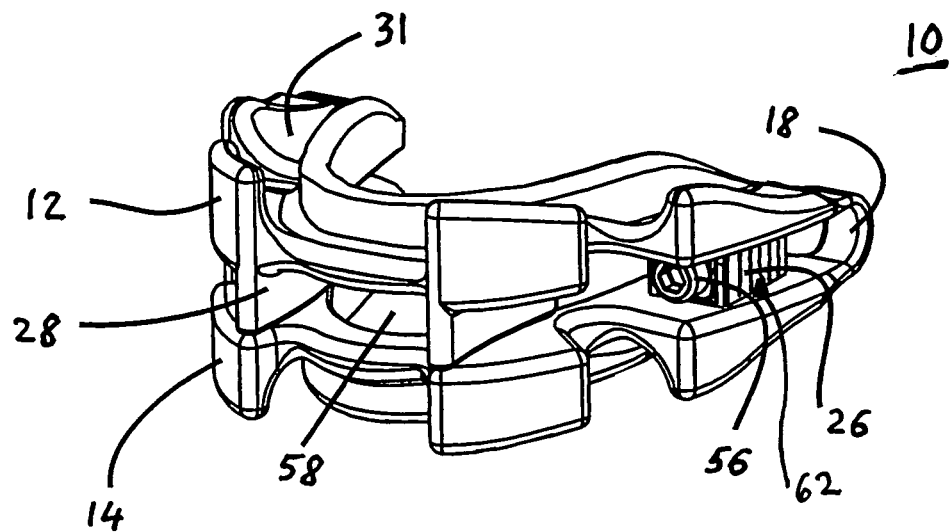
FIG. 3 is a perspective view of the mouthpiece after being assembled according to an embodiment of the present invention.

Referring now to the drawing figures, FIG. 1 shows a bottom perspective view of a mouthpiece 10 according to an embodiment of the present invention. In FIG. 1, the mouthpiece 10 is in an open and flat position prior to being assembled for use. FIG. 2 shows a top plan view of the mouthpiece 10 in the open and flat position. FIG. 3 shows the mouthpiece 10 after it has been assembled.

As shown in FIGS. 1-3, the mouthpiece 10 generally includes an upper guard 12, a lower guard 14, a first adjustable assembly formed by blocks 20 and 24 and screw 54, a second adjustable assembly formed by blocks 22 and 26 and screw 56, and an air passage 58 formed by spacers 28 and 30. The upper guard 12 is configured to fit over the upper teeth or gum of a user and has expandable notches 42, 44, and 46 to allow the upper guard 12 to fit the width of the upper jaw of the user. Similarly, the lower guard 14 is configured to fit over the lower teeth or gum of the user and has expandable notches 48, 50 and 52 to fit the width of the user's lower jaw. The mouthpiece 10 also includes two flexible connectors 16 and 18 for connecting the upper guard 12 to the lower guard 14. When the mouthpiece 10 is the open and flat position as shown in FIGS. 1 and 2, the upper guard 12, the lower guard 14, and the connectors 16 and 18 are coplanar for ease and economy of manufacture.

Details of the features of the mouthpiece 10 will now be described. As shown in FIGS. 1 and 2, the upper guard 12 has substantially an arch shape with a first end connected to connector 16 and a second end connected to connector 18. The bottom surface of the upper guard 12, as shown in FIG. 1, is substantially flat. On the top, as shown in FIG. 2, the upper guard 12 has a trough 31 to fit over the upper teeth or gum of the user. The trough 31 has an inner wall 32 and an outer wall 34. The height of the inner wall 32 is substantially even. In contrast, the height of the outer wall 34 gradually slopes up from the first and second ends toward the center of the arch. Along the center of the trough 31 is a raised strip 33. The trough 31 may be made without the raised strip 33. However, the raised strip 33 may be provided as additional material, preferably thermoplastic, to enhance the formation of the impression of the user's upper teeth.

Furthermore, the outer wall 34 of the upper guard 12 includes a first side notch 42, a second side notch 44, and a middle notch 46. Referring to FIG. 1, the dashed line is a median of the mouthpiece 10. With respect to the median line, the upper guard 12 can be considered as having three sections: a left side, a middle section, and a right side. The first side notch 42 is located between the left side and the middle section of the upper guard 12. The second side notch 44 is located between the middle section and the right side. The middle notch 46 is centered in the middle section. The first side notch 42 and the second side notch 44 are symmetrical with respect to the median line. Each of the notches 42, 44 and 46 looks like a slot being cut into the outer wall 34 and part of the bottom surface of the upper guard 12. From the top plan view of the mouthpiece 10 in FIG. 2, the first and second side notches 42 and 44 have a narrow V shape and the middle notch 46 has a wide U shape.

The lower guard 14 is an inverse of the upper guard 12. As shown in FIGS. 1-2, the lower guard 14 has substantially an arch shape with a first end connected to the connector 16 and a second end connected to the connector 18. The bottom surface of the lower guard 14, as shown in FIG. 1, is substantially flat. On the top as shown in FIG. 2, the lower guard 14 has a trough 36 to fit over the lower teeth or gum of the user. The trough 36 has an inner wall 38 and an outer wall 40. The height of the inner wall 38 is substantially even. In contrast, the height of the outer wall 40 gradually slopes up from the first and second ends toward the center of the arch. Along the center of the trough 36 is a raised strip 39. The trough 36 may be made without the raised strip 39. However, the raised strip 39 may be provided as additional material, preferably thermoplastic, to enhance the formation of the impression of the user's lower teeth.

The lower guard 14 also includes a first side notch 48, a second side notch 50, and a middle notch 52. Referring again to FIG. 1, with respect to the median line, the lower guard 14 can be considered as having three sections: a left side, a middle section, and a right side. The first side notch 48 is located between the left side and the middle section of the lower guard 14. The second side notch 50 is located between the middle section and the right side. The middle notch 52 is centered in the middle section. The first side notch 48 and the second side notch 50 are symmetrical with respect to the dashed median line. Each of the notches 48, 50 and 52 looks like a slot being cut into the outer wall 40 and part of the bottom surface of the lower guard 14. From the top plan view of the mouthpiece 10 in FIG. 2, the side notches 48 and 50 have a narrow V shape and the middle notch 52 has a wide U shape.

As shown in FIG. 3, after the mouthpiece 10 has been assembled, the notches 42, 44 and 46 of the upper guard 12 are substantially aligned with the notches 48, 50 and 52 of the lower guard 14, respectively. The notches 42, 44, 46, 48, 50, and 52 are expandable to allow the upper and lower guards 12 and 14 to become wider or narrower to fit the widths of the user's jaws.

Referring again to FIG. 1, the first and second spacers 28 and 30 are attached to the upper guard 12. More specifically, the first spacer 28 has substantially a V shape and is attached to the bottom surface of the upper guard 12, between the first side notch 42 and the middle notch 46. Similarly, the second spacer 30 has substantially a V shape and is attached to the bottom surface of the upper guard 12, between the middle notch 46 and the second side notch 44. The first and second spacers 28 and 30 are symmetrically positioned with respect to the median line. As shown in FIG. 3, the air passage 58 is formed between the spacers 28 and 30. Although FIG. 1 shows that the spacers 28 and 30 are attached to the upper guard 12, the spacers 28 and 30 may also be attached to the lower guard 14 to obtain the same result, i.e., the air passage 58.

The first adjustable assembly includes blocks 20 and 24 and the first screw 54. The first screw 54 has a cylindrical head and a threaded shank. The cylindrical head of the first screw 54 has a hexagonal socket to be driven by a hexagonal key. Alternatively, other types of screws or heads may be used for the first screw 54. The first adjustable assembly also includes a pointer 60 located near block 20. The pointer 60 is shown in a triangular shape but can be any shape such as round or rectangular.

As shown in FIG. 1, block 20 is attached to the left side of the upper guard 12 and block 24 is attached to the left side of the lower guard 14. Block 20 is a thin, substantially square block and has a non-threaded hole at the center thereof. Block 24 has a channel with two side panels and a middle panel. One of the side panels includes parallel ridges or marks. The middle panel of block 24 has a threaded hole and is located near the first end of the lower guard 14.

When the upper guard 12 is placed over of the lower guard 14, as shown in FIG. 3, block 20 fits inside the channel of block 24 and the non-threaded hole of block 20 lines up with the threaded hole of block 24. The first screw 54 is placed through the non-threaded hole of block 20 and then fastened into the threaded hole of block 24. In addition, the side panel of block 24 that has the parallel ridges is placed between the pointer 60 and block 20. The position of the pointer 60 relative to the parallel ridges on the side panel of block 24 indicates how much the first screw 54 is fastened into the threaded hole of block 24, which allows the user to know how much the lower guard 14 is moved forward with respect to the upper guard 12.

Similar to the first adjustable assembly, the second adjustable assembly includes blocks 22 and 26 and the second screw 56. The second screw 56 has a cylindrical head and a threaded shank. The cylindrical head of the second screw 56 has a hexagonal socket to be driven by a hexagonal key. Alternatively, other types of screws or heads may be used for the second screw 56. The second adjustable assembly also includes a pointer 62 in a triangular shape.

As shown in FIG. 1, block 22 is attached to the right side of the upper guard 12 and block 26 is attached to the right side of the lower guard 14. Block 22 is a thin, substantially square block and has a non-threaded hole at the center thereof. Block 26 has a channel with two side panels and a middle panel. One of the side panels includes parallel ridges or marks. The middle panel of block 26 has a threaded hole and is located near the second end of the lower guard 14.

When the upper guard 12 is placed over of the lower guard 14, block 22 fits inside the channel of block 26 and the non-threaded hole of block 22 lines up with the threaded hole of block 26. The second screw 56 is placed through the non-threaded hole of block 22 and then fastened into the threaded hole of block 26. Moreover, the side panel of block 26 that has the parallel ridges is placed between the pointer 62 and block 22. The position of the pointer 62 relative to the parallel ridges on the side panel of block 26 indicates how much the second screw 56 is fastened into the threaded hole of block 26, which allows the user to know how much the lower guard 14 is moved forward with respect to the upper guard 12.

The first and second adjustable assemblies are symmetrical with respect to the median line in FIG. 1. Blocks 20, 22, 24 and 26 of the first and second adjustable assemblies may, but need not, have substantially the same height as the spacers 28 and 30. As a result, when the mouthpiece 10 is assembled, the upper guard 12 is parallel to the lower guard 14, as shown in FIG. 4.

Referring again to FIG. 3, the assembled mouthpiece 10 is illustrated. To assemble the mouthpiece 10, the mouthpiece 10 that is initially in the open and flat position as shown in FIG. 1 is folded up at the flexible connectors 16 and 18, such that block 20 fits inside the channel of block 24 and block 22 fits inside the channel of block 26. The first screw 54 is inserted through the non-threaded hole of block 20 and fastened to the threaded hole of block 24. Similarly, the second screw 56 is inserted through the non-threaded hole of block 22 and fastened to the threaded hole of block 26.

Figure 4:
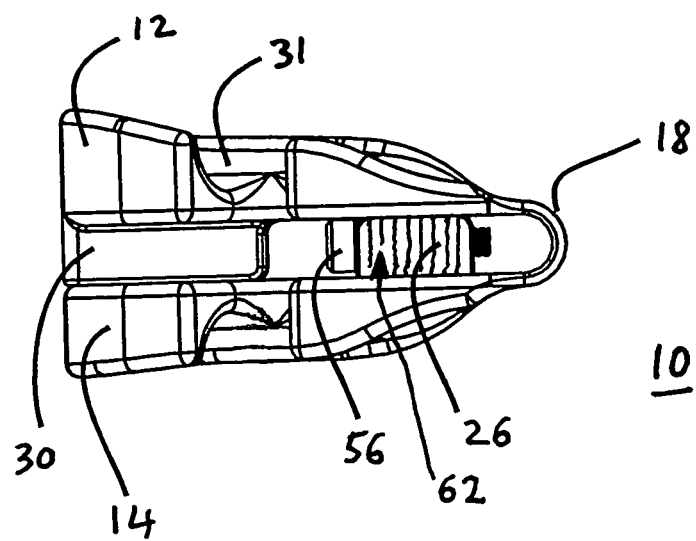
FIG. 4 is a side view of the assembled mouthpiece of FIG. 3 according to an embodiment of the present invention.

FIG. 4 shows a side view of the assembled mouthpiece 10. The spacers 18 and 30 have substantially the same height as the blocks 24 and 26. As a result, the upper guard 12 is parallel to the lower guard 14.

Figure 5:
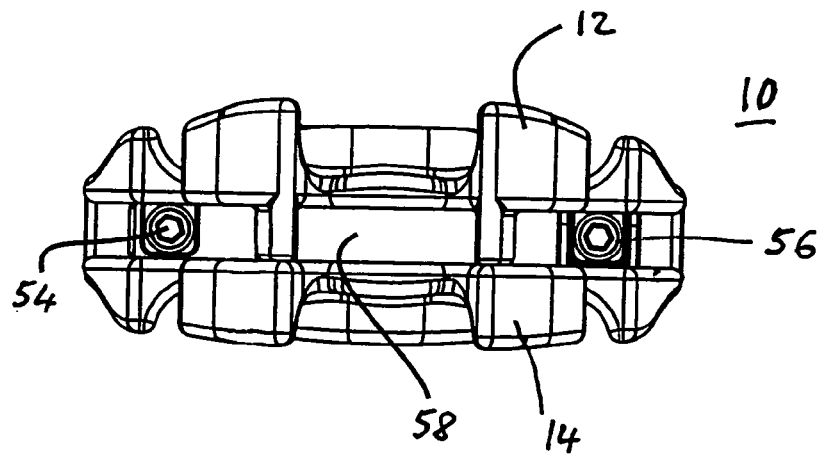
FIG. 5 is a front view of the assembled mouthpiece of FIG. 3 according to an embodiment of the present invention.

FIG. 5 shows a front view of the assembled mouthpiece 10. As seen in FIG. 5, the spacers 28 and 30 create the air passage 58 at the front of the mouthpiece, between the middle sections of the upper guard 12 and the lower guard 14. Furthermore, in FIG. 5, the spacers 28 and 30 are positioned such that the first and second screws 54 and 56 may be driven by a hexagonal key from the front. In an alternative embodiment, the spacers 28 and 30 may be positioned such that the spacers 28 and 30 block the view of the screws 54 and 56 from the front. In such an alternative embodiment, the spacers 28 and 30 prevent the screws 54 and 56 from falling off blocks 20 and 22 when the screws 54 and 56 are not fastened to respective blocks 24 and 26.

In an embodiment, the upper and lower guards 12 and 14 may be thermoplastic, such as EVA. The first and second adjustable assemblies, however, may be made out of a more rigid or thermo-stable material, such as Delrin, so that the threaded holes of blocks 24 and 26 and screws 54 and 56 of the first and second adjustable assemblies remain unchanged in hot water. The connectors 16 and 18 and the spacers 28 and 30 may be made from the same thermoplastic material as the upper and lower guards 12 and 14 or thermo-stable material as the adjustable assemblies. Alternatively, the spacers 28 and 30 may be made from the more rigid, thermo-stable material as blocks 20, 22, 24 and 26.

When the upper and lower guards 12 and 14 are thermoplastic, they can be easily molded to fit the widths of the user's jaws. The molding may be made by placing the assembled mouthpiece 10 of FIG. 3 in hot water. When the mouthpiece 10 softens, the user may insert the mouthpiece 10 in the mouth with the trough 31 fitting over the upper teeth or gum and the trough 36 fitting over the lower teeth or gum. Because the upper and lower guards 12 and 14 are soft, the notches 42, 44, 46, 48, 50, and 52 can be easily expanded or contracted to fit the user's jaws. The user may gently bite into the troughs 31 and 36 to create an imprint of the teeth. The raised strips 33 and 39 in the respective troughs 31 and 36 provide additional materials for the user to bite into to form the impression of the teeth. The user may also press the lips and cheeks against the softened mouthpiece 10 to further adjust the upper and lower guards 12 and 14. After that, the user may remove the mouthpiece 10 and adjust the screws 54 and 56.

The screws 54 and 56 may be tightened to adjust the position of the lower guard 14 relative to the upper guard 12. The more the screws 54 and 56 are fastened into the respective threaded holes of blocks 24 and 26, the more the lower guard 14 moves out towards the front of the mouth. In an embodiment, the maximum the lower guard 14 may move outward is approximately 8 mm.

With the lower guard 14 being moved outward relative to the upper guard 12, the lower jaw of the user will be brought out toward the front of the mouth relative to the upper jaw when the mouthpiece 10 is in use. As a result, the mouthpiece 10 opens the normally restricted airway and allows the user to breathe more easily during sleep, causing reduction of snoring. The mouthpiece 10 may also be used as a mouth guard for grinding teeth.

Figure 6:
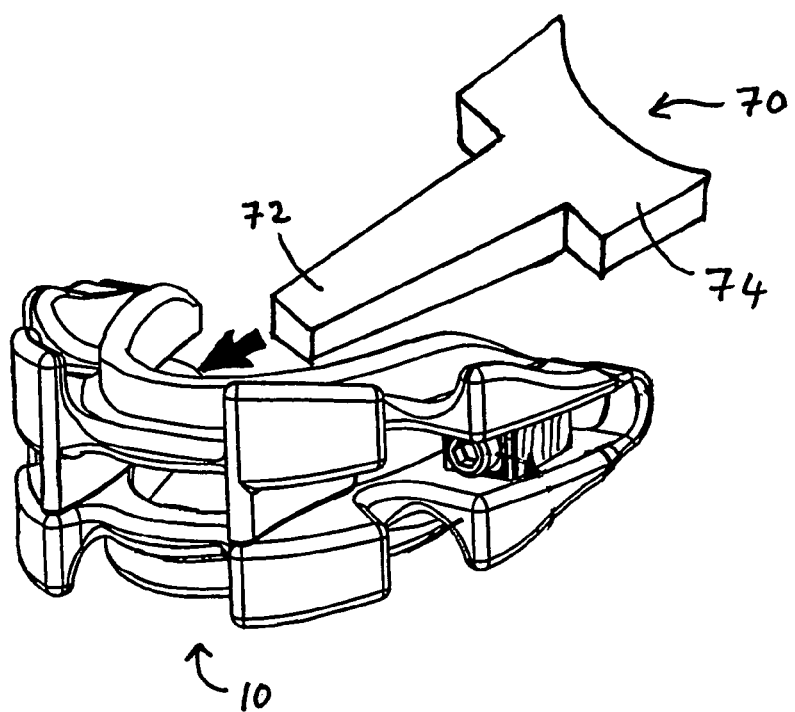
FIG. 6 illustrates the assembled mouthpiece of FIG. 3 and a separating device according to an embodiment of the present invention.

FIG. 6 shows a combination of the mouthpiece 10 and a separating device 70, according to another embodiment of the present invention. The separating device 70 may be used during the molding of the mouthpiece 10 to fit the user's jaws.

The separating device 70 is an elongated device having a first end 72 and a second end 74. The first end 72 is narrower than the air passage 58 of the mouthpiece 10 and the second end 74 is wider than the air passage 58. The separating device 70 is made from a plastic material that is more rigid or harder than the plastic of the spacers 28 and 30.

In operation, when the assembled mouthpiece 10 softens, the user may insert the first end 72 of the separating device 70 through the air passage 58 from the inner side of the arch of the mouthpiece 10. The first end 72 intrudes to the front of the mouthpiece 10. The user then places the mouthpiece 10 into the mouth while holding the first end 72. Because the separating device 70 is rigid, it keeps the upper guard 12 separated from the lower guard 14 while the user bites into the softened troughs 31 and 32. After the mouthpiece 10 is molded to fit the user's jaws, the user may remove the mouthpiece 10 from the mouth and adjust the screws 54 and 56 as described above.

It is to be understood that the above detailed description of the embodiments of the invention is provided by way of example only. Various details of design, construction and procedure may be modified without departing from the spirit and scope of the invention, as set forth in the appended claims.

What is claimed is:

1. A mouthpiece comprising:
   an upper element configured to fit over the upper teeth or gum of a user, wherein the upper element includes a left side, a middle section, and a right side;
   a lower element configured to fit over the lower teeth or gum of the user, wherein the lower element includes a left side, a middle section, and a right side; wherein the upper and lower element have a substantially arch shape having a first end and a second end; a first connector connected to the first end of the upper element and the first end of the lower element; and a second connector connected to the second end of the upper element and the second end of the lower element;
   a spacer assembly attached to at least one of the upper element and the lower element, and configured to provide an air passage between the middle section of the upper element and the middle section of the lower element, the spacer assembly including a first portion located substantially between the left side and the middle section of the upper element and a second portion located substantially between the right side and the middle section of the upper element;
   a first adjustable assembly attached to the left side of the upper element and the left side of the lower element; and
   a second adjustable assembly attached to the right side of the upper element and the right side of the lower element,
   wherein the first adjustable assembly and the second adjustable assembly are operable to move the lower element relative to the upper element, the first adjustable assembly further includes a first pointer for indicating a position of the left side of the upper element in relation with the left side of the lower element and the second adjustable assembly further includes a second pointer for indicating a position of the right side of the upper element in relation with the right side of the lower element.

2. The mouthpiece of claim 1, wherein the upper element further includes:
   a first notch located between the left side and the middle section of the upper element;
   a second notch located in the middle section of the upper element; and
   a third notch located between the middle section and the right side of the upper element; and
   wherein the lower element further includes:
   a fourth notch located between the left side and the middle section of the lower element;
   a fifth notch located in the middle section of the lower element; and
   a sixth notch located between the middle section and the right side of the lower element.

3. The mouthpiece of claim 2, wherein the first adjustable assembly includes:
   a first upper block attached to the left side of the upper element, wherein the first upper block includes a hole;
   a first lower block attached to the left side of the lower element, wherein the first lower block includes a threaded hole; and
   a first screw inserted through the hole of the first upper block and fastened to the threaded hole of the first lower block; and
   wherein the second adjustable assembly includes:
   a second upper block attached to the right side of the upper element, wherein the second upper block includes a hole;

a second lower block attached to the right side of the lower element, wherein the second lower block includes a threaded hole; and a second screw inserted through the hole of the upper block and the threaded hole of the second lower block.

4. The mouthpiece of claim 3, wherein the first lower block of the first adjustable assembly has a channel, and the first upper block of the first adjustable assembly fits inside the channel of the first lower block; and wherein the second lower block of the second adjustable assembly has a channel, and the second upper block of the second adjustable assembly fits inside the channel of the second lower block.

5. The mouthpiece of claim 4, wherein the first portion of the spacer assembly includes a first V-shaped raised portion attached to the upper element, and located between the first notch and the second notch; and the second portion of the spacer assembly includes a second V-shaped raised portion attached to the upper element, and located between the second notch and the third notch.

6. The mouthpiece of claim 5, wherein the upper element further includes a first raised strip for the user to bite the upper teeth into, and wherein the lower element further includes a second raised strip for the user to bite the lower teeth into.

7. A mouthpiece comprising:

an upper element configured to fit over the upper teeth or gum of a user, wherein the upper element includes:
 a left side, a middle section, and a right side;
 a first notch located between the left side and the middle section of the upper element;
 a second notch located in the middle section of the upper element; and
 a third notch located between the middle section and the right side of the upper element;

a lower element configured to fit over the lower teeth or gum of the user, wherein the lower element includes:
 a left side, a middle section, and a right side;
 a fourth notch located between the left side and the middle section of the lower element;
 a fifth notch located in the middle section of the lower element; and
 a sixth notch located between the middle section and the right side of the lower element; wherein the upper and lower element have a substantially arch shape having a first end and a second end; a first connector connected to the first end of the upper element and the first end of the lower element; and a second connector connected to the second end of the upper element and the second end of the lower element; and a spacer assembly attached to at least one of the upper element and the lower element, and configured to provide an air passage between the middle section of the upper element and the middle section of the lower element, the spacer assembly including a first portion located between the first notch and the second notch and a second portion located between the second notch and the third notch.

8. The mouthpiece of claim 7, further comprising:

a first adjustable assembly including:
 a first upper block attached to the left side of the upper element, wherein the first upper block includes a hole;
 a first lower block attached to the left side of the lower element, wherein the first lower block includes a threaded hole; and
 a first screw inserted through the hole of the first upper block and fastened to the threaded hole of the first lower block;

a second adjustable assembly including:
 a second upper block attached to the right side of the upper element, wherein the second upper block includes a hole;
 a second lower block attached to the right side of the lower element, wherein the second lower block includes a threaded hole; and
 a second screw inserted through the hole of the second upper block and the threaded hole of the second lower block;

a first connector connected to a first end of the upper element and a first end of the lower element; and a second connector connected to a second end of the upper element and a second end of the lower element, wherein a height of the spacer assembly is equal to a height of the first and second lower blocks of the first and second adjustable assemblies, the first adjustable assembly and the second adjustable assembly are operable to move the lower element relative to the upper element, wherein the first adjustable assembly further includes a first pointer for indicating a position of the first screw in relation with the first lower block and the second adjustable assembly further includes a second pointer for indicating a position of the second screw in relation with the second lower block.

9. A mouthpiece comprising:

an upper element configured to fit over the upper teeth or gum of a user, wherein the upper element includes:
 a left side, a middle section, and a right side;
 a first notch located between the left side and the middle section of the upper element;
 a second notch located in the middle section of the upper element; and
 a third notch located between the middle section and the right side of the upper element;

a lower element configured to fit over the lower teeth or gum of the user, wherein the lower element includes:
 a left side, a middle section, and a right side;
 a fourth notch located between the left side and the middle section of the lower element;
 a fifth notch located in the middle section of the lower element; and
 a sixth notch located between the middle section and the right side of the lower element; wherein the upper and lower element have a substantially arch shape having a first end and a second end; a first connector connected to the first end of the upper element and the first end of the lower element; and a second connector connected to the second end of the upper element and the second end of the lower element;

a spacer assembly attached to at least one of the upper element and the lower element, and configured to provide an air passage between the middle section of the upper element and the middle section of the lower element, the spacer assembly including a first portion located between the first notch and the second notch and a second portion located between the second notch and the third notch;

a first adjustable assembly attached to the left side of the upper element and the left side of the lower element; and a second adjustable assembly attached to the right side of the upper element and the right side of the lower element, wherein the first adjustable assembly and the second adjustable assembly are operable to move the lower element relative to the upper element, wherein the first adjustable assembly further includes a first pointer for indicating a position of the left side of the upper element in relation with the left side of the lower element and the second adjustable assembly further includes a second pointer for indicating a position of the right side of the upper element in relation with the right side of the lower element.

10. The mouthpiece of claim 9, wherein the first adjustable assembly includes:
   a first upper block attached to the left side of the upper element, wherein the upper block includes a hole;
   a first lower block attached to the left side of the lower element, wherein the first lower block includes a threaded hole; and
   a first screw inserted through the hole of the first upper block and fastened to the threaded hole of the first lower block; and
wherein the second adjustable assembly includes:
a second upper block attached to the right side of the upper element, wherein the second upper block includes a hole;
a second lower block attached to the right side of the lower element, wherein the second lower block includes a threaded hole; and
a second screw inserted through the hole of the second upper block and the threaded hole of the second lower block.

11. The mouthpiece of claim 10, wherein the first lower block has a channel, and the first upper block fits inside the channel of the first lower block; and
   wherein the second lower block has a channel, and the second upper block fits inside the channel of the second lower block.

12. The mouthpiece of claim 11, wherein the first and second lower blocks include ridges.

13. The mouthpiece of claim 12, wherein the first portion of the spacer assembly includes a first raised portion attached to the upper element; and
   the second portion of the spacer assembly includes a second raised portion attached to the upper element.

14. The mouthpiece of claim 13, wherein the first raised portion has a substantially V shape and the second raised portion has a substantially V shape.

15. The mouthpiece of claim 14, wherein a height of the first and second raised portions is equal to a height of the first and second lower blocks of the first and second adjustable assemblies.

16. The mouthpiece of claim 9, wherein the upper element further includes a first raised strip for the user to bite the upper teeth into, and wherein the lower element further includes a second raised strip for the user to bite the lower teeth into.

17. The mouthpiece of claim 9, wherein the upper and lower elements, the spacer assembly, and the first and second connectors are thermoplastic; and wherein the first and second adjustable assemblies are thermo-stable.

* * * * *